United States Patent
Xu et al.

(10) Patent No.: US 7,981,481 B2
(45) Date of Patent: Jul. 19, 2011

(54) METHOD FOR CONTROLLING DISTRIBUTION OF FLUID COMPONENTS ON A BODY

(75) Inventors: Frank Xu, Round Rock, TX (US); Ian McMackin, Austin, TX (US); PanKaj B. Lad, DeSoto, TX (US); Michael P. C. Watts, Austin, TX (US)

(73) Assignee: Molecular Imprints, Inc., Austin, TX (US)

( * ) Notice: Subject to any disclaimer, the term of this patent is extended or adjusted under 35 U.S.C. 154(b) by 1094 days.

(21) Appl. No.: 11/608,374

(22) Filed: Dec. 8, 2006

(65) Prior Publication Data

US 2007/0141271 A1 Jun. 21, 2007

Related U.S. Application Data

(63) Continuation-in-part of application No. 10/948,511, filed on Sep. 23, 2004, now abandoned.

(51) Int. Cl.
*C08F 2/48* (2006.01)
(52) U.S. Cl. .................................................... 427/508
(58) Field of Classification Search .................. 427/508
See application file for complete search history.

(56) References Cited

U.S. PATENT DOCUMENTS

| | | |
|---|---|---|
| 3,810,874 A | 5/1974 | Mitsch et al. |
| 3,919,351 A | 11/1975 | Chang et al. |
| 4,271,258 A | 6/1981 | Watariguchi |
| 4,512,848 A | 4/1985 | Deckman et al. |
| 4,514,439 A | 4/1985 | Rounds |
| 4,517,337 A | 5/1985 | Lockhart et al. |
| 4,544,572 A | 10/1985 | Sandvig et al. |
| 4,552,833 A | 11/1985 | Ito et al. |
| 4,614,667 A | 9/1986 | Larson et al. |
| 4,617,238 A | 10/1986 | Crivello et al. |
| 4,687,707 A | 8/1987 | Matsuo et al. |
| 4,722,878 A | 2/1988 | Watakabe et al. |
| 4,731,155 A | 3/1988 | Napoli et al. |
| 4,808,511 A | 2/1989 | Holmes |
| 4,826,943 A | 5/1989 | Ito et al. |

(Continued)

FOREIGN PATENT DOCUMENTS

JP 61-40845 2/1986

(Continued)

OTHER PUBLICATIONS

Hu et al., Fluorescence Probe Techniques (FPT) for Measuring the Relative Efficiencies of Free-Radical Photoinitiators, Macromolecules 1998, 31, pp. 4107-4113 May 29, 1998.

(Continued)

*Primary Examiner* — Elena T Lightfoot
(74) *Attorney, Agent, or Firm* — Fish & Richardson P.C.; Heather Flanagan (57) ABSTRACT

The present invention provides a method of controlling the distribution of a fluid on a body that features compensating for varying distribution of constituent components of a composition that moved over a surface of a substrate. To that end, the method includes generating a sequence of patterns of liquid upon a substrate, each of which includes a plurality of spaced-apart liquid regions, with voids being defined between adjacent liquid regions. A second of the patterns of liquid of the sequence is arranged so that the liquid regions associated therewith are in superimposition with the voids of a first of the patterns of liquid of the sequence.

19 Claims, 4 Drawing Sheets

U.S. PATENT DOCUMENTS

| | | | |
|---|---|---|---|
| 4,931,351 A | 6/1990 | McColgin et al. |
| 4,959,252 A | 9/1990 | Bonnebat et al. |
| 4,988,274 A | 1/1991 | Kenmochi |
| 5,028,366 A | 7/1991 | Harakal et al. |
| 5,028,511 A | 7/1991 | Choi |
| 5,108,875 A | 4/1992 | Thackeray et al. |
| 5,110,514 A | 5/1992 | Soane |
| 5,169,494 A | 12/1992 | Hashimoto et al. |
| 5,170,182 A | 12/1992 | Olson et al. |
| 5,170,192 A | 12/1992 | Pettigrew et al. |
| 5,180,757 A | 1/1993 | Lucey |
| 5,204,381 A | 4/1993 | Zeigler |
| 5,206,983 A | 5/1993 | Guckel et al. |
| 5,234,793 A | 8/1993 | Sebald et al. |
| 5,240,550 A | 8/1993 | Boehnke et al. |
| 5,242,711 A | 9/1993 | DeNatale et al. |
| 5,259,926 A | 11/1993 | Kuwabara et al. |
| 5,298,556 A | 3/1994 | Stephens |
| 5,302,627 A | 4/1994 | Field et al. |
| 5,314,731 A | 5/1994 | Yoneda et al. |
| 5,318,870 A | 6/1994 | Hartney |
| 5,331,020 A | 7/1994 | Brown et al. |
| 5,369,722 A | 11/1994 | Heming et al. |
| 5,389,696 A | 2/1995 | Dempsey et al. |
| 5,395,954 A | 3/1995 | Soria et al. |
| 5,417,802 A | 5/1995 | Obeng |
| 5,425,848 A | 6/1995 | Haisma et al. |
| 5,439,766 A | 8/1995 | Day et al. |
| 5,459,198 A | 10/1995 | Sharp |
| 5,462,700 A | 10/1995 | Beeson et al. |
| 5,480,047 A | 1/1996 | Tanigawa et al. |
| 5,482,768 A | 1/1996 | Kawasato et al. |
| 5,512,131 A | 4/1996 | Kumar et al. |
| 5,523,878 A | 6/1996 | Wallace et al. |
| 5,527,662 A | 6/1996 | Hashimoto et al. |
| 5,542,978 A | 8/1996 | Kindt-Larsen et al. |
| 5,545,367 A | 8/1996 | Bae et al. |
| 5,594,042 A | 1/1997 | Glover et al. |
| 5,601,641 A | 2/1997 | Stephens |
| 5,629,095 A | 5/1997 | Bujanowski et al. |
| 5,629,128 A | 5/1997 | Shirakawa et al. |
| 5,669,303 A | 9/1997 | Maracas et al. |
| 5,723,242 A | 3/1998 | Woo et al. |
| 5,725,788 A | 3/1998 | Maracas et al. |
| 5,772,905 A | 6/1998 | Chou |
| 5,776,748 A | 7/1998 | Singhvi et al. |
| 5,820,769 A | 10/1998 | Chou |
| 5,837,314 A | 11/1998 | Beaton et al. |
| 5,849,209 A | 12/1998 | Kindt-Larsen et al. |
| 5,849,222 A | 12/1998 | Jen et al. |
| 5,861,467 A | 1/1999 | Bujanowski et al. |
| 5,888,650 A | 3/1999 | Calhoun et al. |
| 5,895,263 A | 4/1999 | Carter et al. |
| 5,905,104 A | 5/1999 | Eklund et al. |
| 5,948,470 A | 9/1999 | Harrison et al. |
| 5,956,216 A | 9/1999 | Chou |
| 6,046,056 A | 4/2000 | Parce et al. |
| 6,063,888 A | 5/2000 | Yamaguchi et al. |
| 6,066,269 A | 5/2000 | Wei et al. |
| 6,074,827 A | 6/2000 | Nelson et al. |
| 6,114,404 A | 9/2000 | Deeken et al. |
| 6,117,708 A | 9/2000 | Wensel |
| 6,132,632 A | 10/2000 | Haney et al. |
| 6,174,931 B1 | 1/2001 | Moon et al. |
| 6,190,929 B1 | 2/2001 | Wang et al. |
| 6,200,736 B1 | 3/2001 | Tan |
| 6,204,343 B1 | 3/2001 | Barucha et al. |
| 6,218,316 B1 | 4/2001 | Marsh |
| 6,261,469 B1 | 7/2001 | Zakhidov et al. |
| 6,274,294 B1 | 8/2001 | Hines |
| 6,309,580 B1 | 10/2001 | Chou |
| 6,316,290 B1 | 11/2001 | Wensel |
| 6,326,627 B1 | 12/2001 | Putvinski et al. |
| 6,334,960 B1 | 1/2002 | Willson et al. |
| 6,335,149 B1 | 1/2002 | Xu et al. |
| 6,342,097 B1 | 1/2002 | Terry et al. |
| 6,344,105 B1 | 2/2002 | Daugherty et al. |
| 6,348,999 B1 | 2/2002 | Summersgill et al. |
| 6,355,198 B1 | 3/2002 | Kim et al. |
| 6,391,217 B2 | 5/2002 | Schaffer et al. |
| 6,399,406 B2 | 6/2002 | Chan et al. |
| 6,446,933 B1 | 9/2002 | Westmoreland |
| 6,468,642 B1 | 10/2002 | Bray et al. |
| 6,468,896 B2 | 10/2002 | Rohr et al. |
| 6,475,704 B1 | 11/2002 | Iwasaki et al. |
| 6,482,742 B1 | 11/2002 | Chou |
| 6,497,961 B2 | 12/2002 | Kang et al. |
| 6,503,914 B1 | 1/2003 | Benish et al. |
| 6,517,977 B2 | 2/2003 | Resnick et al. |
| 6,517,995 B1 | 2/2003 | Jacobson et al. |
| 6,518,168 B1 | 2/2003 | Clem et al. |
| 6,518,189 B1 | 2/2003 | Chou |
| 6,541,356 B2 | 4/2003 | Fogel et al. |
| 6,544,594 B2 | 4/2003 | Linford et al. |
| 6,565,776 B1 | 5/2003 | Li et al. |
| 6,580,172 B2 | 6/2003 | Mancini et al. |
| 6,583,248 B1 | 6/2003 | Bowen |
| 6,600,207 B2 | 7/2003 | Huang et al. |
| 6,605,849 B1 | 8/2003 | Lutwak et al. |
| 6,607,173 B2 | 8/2003 | Westmoreland |
| 6,646,662 B1 | 11/2003 | Nebashi et al. |
| 6,649,272 B2 | 11/2003 | Moore et al. |
| 6,664,026 B2 | 12/2003 | Nguyen et al. |
| 6,664,306 B2 | 12/2003 | Gaddam et al. |
| 6,696,157 B1 | 2/2004 | David et al. |
| 6,696,220 B2 | 2/2004 | Bailey et al. |
| 6,713,238 B1 | 3/2004 | Chou et al. |
| 6,721,529 B2 | 4/2004 | Chen et al. |
| 6,737,489 B2 | 5/2004 | Linert et al. |
| 6,774,183 B1 | 8/2004 | Palumbo et al. |
| 6,776,094 B1 | 8/2004 | Whitesides et al. |
| 6,790,905 B2 | 9/2004 | Fitzgerald et al. |
| 6,802,870 B2 | 10/2004 | Chang et al. |
| 6,809,356 B2 | 10/2004 | Chou |
| 6,828,244 B2 | 12/2004 | Chou |
| 6,830,819 B2 | 12/2004 | Kaplan et al. |
| 6,842,229 B2 | 1/2005 | Sreenivasan et al. |
| 6,849,558 B2 | 2/2005 | Schaper |
| 6,871,558 B2 | 3/2005 | Choi et al. |
| 6,900,881 B2 | 5/2005 | Sreenivasan et al. |
| 6,908,861 B2 | 6/2005 | Sreenivasan et al. |
| 6,916,584 B2 | 7/2005 | Sreenivasan et al. |
| 6,916,585 B2 | 7/2005 | Sreenivasan et al. |
| 6,926,929 B2 | 8/2005 | Watts et al. |
| 6,932,934 B2 | 8/2005 | Choi et al. |
| 6,936,194 B2 | 8/2005 | Watts |
| 6,980,282 B2 | 12/2005 | Choi et al. |
| 6,990,870 B2 | 1/2006 | Choi et al. |
| 7,019,819 B2 | 3/2006 | Choi et al. |
| 7,036,389 B2 | 5/2006 | Choi et al. |
| 7,037,639 B2 | 5/2006 | Voisin |
| 7,071,088 B2 | 7/2006 | Watts et al. |
| 7,077,992 B2 | 7/2006 | Sreenivasan et al. |
| 7,090,716 B2 | 8/2006 | McMackin et al. |
| 7,122,079 B2 | 10/2006 | Xu et al. |
| 7,122,482 B2 | 10/2006 | Xu et al. |
| 7,138,362 B2 | 11/2006 | Abe et al. |
| 7,141,188 B2 | 11/2006 | Li et al. |
| 7,157,036 B2 | 1/2007 | Choi et al. |
| 7,179,079 B2 | 2/2007 | Sreenivasan et al. |
| 7,244,386 B2 | 7/2007 | Sreenivasan et al. |
| 7,252,715 B2 | 8/2007 | Watts et al. |
| 7,270,533 B2 | 9/2007 | McMackin et al. |
| 7,281,919 B2 | 10/2007 | Shackleton et al. |
| 7,298,456 B2 | 11/2007 | Cherala et al. |
| 7,316,554 B2 | 1/2008 | Choi et al. |
| 7,338,275 B2 | 3/2008 | Choi et al. |
| 7,360,851 B1 | 4/2008 | Snyder |
| 7,462,028 B2 | 12/2008 | Cherala et al. |
| 7,473,090 B2 | 1/2009 | McMackin et al. |
| 2001/0044075 A1 | 11/2001 | Nishimura et al. |
| 2002/0042027 A1 | 4/2002 | Chou et al. |
| 2002/0115002 A1* | 8/2002 | Bailey et al. ............ 430/5 |
| 2002/0132482 A1 | 9/2002 | Chou |
| 2002/0167117 A1 | 11/2002 | Chou |
| 2002/0177319 A1 | 11/2002 | Chou |
| 2003/0034329 A1 | 2/2003 | Chou |

| | | | |
|---|---|---|---|
| 2003/0054115 A1 | 3/2003 | Albano et al. | |
| 2003/0062334 A1 | 4/2003 | Lee et al. | |
| 2003/0080471 A1 | 5/2003 | Chou | |
| 2003/0080472 A1 | 5/2003 | Chou | |
| 2003/0129542 A1 | 7/2003 | Shih et al. | |
| 2003/0166814 A1 | 9/2003 | Sparrowe et al. | |
| 2003/0235787 A1 | 12/2003 | Watts et al. | |
| 2004/0036201 A1 | 2/2004 | Chou et al. | |
| 2004/0046288 A1 | 3/2004 | Chou | |
| 2004/0065252 A1 | 4/2004 | Sreenivasan et al. | |
| 2004/0065976 A1 | 4/2004 | Sreenivasan et al. | |
| 2004/0110856 A1 | 6/2004 | Young et al. | |
| 2004/0112862 A1 | 6/2004 | Willson et al. | |
| 2004/0116548 A1 | 6/2004 | Willson et al. | |
| 2004/0118809 A1 | 6/2004 | Chou et al. | |
| 2004/0131718 A1 | 7/2004 | Chou et al. | |
| 2004/0137734 A1 | 7/2004 | Chou et al. | |
| 2004/0156108 A1 | 8/2004 | Chou et al. | |
| 2004/0163563 A1 | 8/2004 | Sreenivasan et al. | |
| 2004/0170770 A1 | 9/2004 | Nguyen et al. | |
| 2004/0192041 A1 | 9/2004 | Jeong et al. | |
| 2004/0197843 A1 | 10/2004 | Chou et al. | |
| 2004/0202872 A1 | 10/2004 | Fang et al. | |
| 2004/0241338 A1 | 12/2004 | Foster et al. | |
| 2004/0250945 A1 | 12/2004 | Zheng et al. | |
| 2005/0037143 A1 | 2/2005 | Chou et al. | |
| 2005/0061773 A1 | 3/2005 | Choi et al. | |
| 2005/0072757 A1 | 4/2005 | McMackin et al. | |
| 2005/0084804 A1 | 4/2005 | Truskett et al. | |
| 2005/0106321 A1 | 5/2005 | McMackin et al. | |
| 2005/0113484 A1 | 5/2005 | Kamen et al. | |
| 2005/0118749 A1 | 6/2005 | Sakamoto et al. | |
| 2005/0156357 A1 | 7/2005 | Willson et al. | |
| 2005/0189676 A1 | 9/2005 | Sreenivasan | |
| 2005/0236739 A1 | 10/2005 | Willson et al. | |
| 2005/0270312 A1 | 12/2005 | Lad et al. | |
| 2005/0276919 A1 | 12/2005 | Truskett et al. | |
| 2006/0035029 A1 | 2/2006 | Xu et al. | |
| 2006/0036051 A1 | 2/2006 | Xu et al. | |
| 2006/0062867 A1 | 3/2006 | Choi et al. | |
| 2006/0062922 A1 | 3/2006 | Xu et al. | |
| 2006/0063112 A1 | 3/2006 | Sreenivasan | |
| 2006/0076717 A1 | 4/2006 | Sreenivasan et al. | |
| 2006/0077374 A1 | 4/2006 | Sreenivasan et al. | |
| 2006/0081557 A1 | 4/2006 | Xu et al. | |
| 2006/0108710 A1 | 5/2006 | Xu et al. | |
| 2006/0115999 A1 | 6/2006 | Sreenivasan et al. | |
| 2006/0121728 A1 | 6/2006 | McMackin et al. | |
| 2006/0145398 A1 | 7/2006 | Bailey et al. | |
| 2006/0175736 A1 | 8/2006 | Xu et al. | |
| 2006/0177532 A1 | 8/2006 | Fletcher et al. | |
| 2006/0177535 A1 | 8/2006 | McMackin et al. | |
| 2007/0017631 A1 | 1/2007 | Xu | |
| 2007/0063384 A1 | 3/2007 | Choi et al. | |
| 2007/0114686 A1 | 5/2007 | Choi et al. | |
| 2007/0126150 A1 | 6/2007 | GanapathiSubramanian et al. | |
| 2007/0132152 A1 | 6/2007 | Choi et al. | |
| 2007/0170617 A1 | 7/2007 | Choi et al. | |
| 2007/0228593 A1 | 10/2007 | Jones et al. | |
| 2007/0228608 A1 | 10/2007 | Shackleton et al. | |
| 2007/0228610 A1 | 10/2007 | Sreenivasan et al. | |
| 2008/0085465 A1 | 4/2008 | Xu et al. | |
| 2008/0141862 A1 | 6/2008 | Xu et al. | |
| 2008/0153312 A1 | 6/2008 | Sreenivasan et al. | |
| 2008/0174046 A1 | 7/2008 | Choi et al. | |
| 2008/0199816 A1 | 8/2008 | Choi et al. | |
| 2008/0303187 A1 | 12/2008 | Stacey et al. | |

FOREIGN PATENT DOCUMENTS

| | | |
|---|---|---|
| JP | 1-196749 | 8/1989 |
| JP | 02-24848 | 1/1990 |
| JP | 02-92603 | 4/1990 |
| JP | 02192045 | 7/1990 |
| JP | 2-248480 | 10/1990 |
| JP | 3-90345 | 4/1991 |
| JP | 9-278490 | 10/1997 |
| WO | WO 87/02935 | 5/1987 |
| WO | WO 99/05724 | 2/1999 |
| WO | WO 00/21689 | 4/2000 |
| WO | WO 01/47003 | 6/2001 |
| WO | WO 02/07199 A | 1/2002 |
| WO | WO 03/010289 A2 | 2/2003 |
| WO | WO 03/079416 A | 9/2003 |
| WO | WO 03/099536 A | 12/2003 |

OTHER PUBLICATIONS

Johnson et al., Advances in Step and Flash Imprint Lithography, SPIE Microlithography Conference Feb. 23, 2003.

Chou et al., Lithographically Induced Self-assembly of Periodic Polymer Micropillar Arrays, J. Vac. Sci. Technol. B 17 (6), pp. 3197-3202 Nov. 1, 1999.

Colburn et al., Step and Flash Imprint Lithography: A New Approach to High-Resolution Patterning, Proc. Of SPIE, vol. 3676 Mar. 1, 1999.

Kotachi et al., Si-Containing Positive Resist for ArF Excimer Laser Lithography, Photopolymer Science and Technology, pp. 615-622 Nov. 4, 1995.

Chou, Nanoimprint Lithography and Lithographically Induced Self-Assembly, MRS Bulletin, pp. 512-517 Jul. 1, 2001.

Choi et al., Design of Orientation Stages for Step and Flash Imprint Lithography, Precision Engineering, pp. 192-199 Jan. 1, 2001.

Cowie, Polymers: Chemistry and Physics of Modern Materials, 2nd Ed. Jan. 1, 1991.

Xia et al., Soft Lithography, Angew. Chem. Int. Ed., pp. 550-575 Jan. 1, 1998.

Chou et al., Imprint Lithography with Sub-10 nm Feature Size and High Throughput, Microelectronic Engineering 35, pp. 237-240 Jan. 1, 1997.

Haisma et al., Mold-assisted Nanolithography: A Process for Reliable Pattern Replication, J. Vac. Sci. Technol. B, pp. 4124-4128 Nov. 1, 1996.

Chou et al., Imprint of Sub-25 nm Vias and Trenches in Polymers, Appl. Phys. Lett. 67 (21) Nov. 20, 1995.

Krug et al., Fine Patterning of Thin Sol-gel Films, Journal of Non-Crystalline Solids 147 & 148, pp. 447-450 Jan. 1, 1992.

Bender et al., Fabrication of Nanostructures using a UV-based Imprint Technique, Microelectronic Engineering 53, pp. 233-236 Jan. 1, 2000.

Nguyen, Asymmetric Fluid-Structure Dynamics in Nanoscale Imprint Lithography, The University of Texas at Austin, pp. 1-111 Aug. 1, 2001.

Eldada et al., Robust Photopolymers for MCM, Board, and Backplane Optical Interconnects, SPIE vol. 3288, pp. 175-191 Jan. 1, 1998.

Eldada et al., Affordable WDM Components: The Polymer Solution, SPIE vol. 3234, pp. 161-174 Jan. 1, 1998.

Eldada et al., Advanced Polymer Systems for Optoelectronic Integrated Circuit Applications, SPIE vol. 3006, pp. 344-361 Jan. 1, 1997.

Bender et al., Multiple Imprinting in UV-based Nanoimprint Lithography: Related Material Issues, Microelectronic Engineering 61-62, pp. 407-413 Jan. 1, 2002.

Colburn et al., Step and Flash Imprint Lithography for sub-100 nm Patterning, Proceedings of SPIE vol. 3997, pp. 453-457 Jan. 1, 2000.

Chou et al., Imprint Lithography with 25-Nanometer Resolution, Science vol. 272, pp. 85-87 Apr. 5, 1996.

Heidari, Nanoimprint Lithography at the 6 in. Wafer Scale, J. Vac. Sci. Technol. B 18(6), pp. 3557-3560 Nov. 1, 2000.

Abstract of Japanese Patent 02-92603, Aug. 12, 2004.

Translation of Japanese Patent 02-92603, Apr. 3, 1990.

Translation of Japanese Patent 02-24848, Jan. 26, 1990.

Abstract of Japanese Patent 02-24848, Jan. 26, 1990.

Hirai et al., Mold Surface Treatment for Imprint Lithography, Journal of Photopolymer Science and Technology, vol. 14, No. 3, pp. 457-462 Aug. 1, 2001.

Parikh et al., An Intrinsic Relationship between Molecular Structure in Self-Assembled n-Alkylsiloxane Monolayers and Deposition Temperature, Journal of Phys. Chem., pp. 7577-7590 Jul. 1, 1994.

Sagiv, Organized Monolayers by Absorption. 1. Formation and Structure of Oleophobic Mixed Monolayers on Solid Surfaces, Journal of the American Chemical Society/102:1 Jan. 2, 1980.

Roos et al., Nanoimprint Lithography with a Commercial 4 Inch Bond System for Hot embossing, Proceedings of SPIE vol. 4343, pp. 427-435 Oct. 1, 2001.

Roos et al., Abstract of Nanoimprint Lithography with a Commercial 4 Inch Bond System for Hot Embossing, Proceedings of SPIE vol. 4343, pp. 427-435 Oct. 1, 2001.

Srinivasan et al., Alkyltrichlorosilane-Based Self-Assembled Monolayer Films for Stiction Reduction in Silicon Micromachines, Journal of Microelectromechanical Systems, vol. 7, No. 2, p. 252-260 Jun. 1, 1998.

Kim et al., Surface Energy and Polarity of Treated Indium-Tin-Oxide Anodes for Polymer Light-Emitting Diodes Studied by Contact-Angle Measurements, Journal of Applied Physics, vol. 86, No. 5, pp. 2774-2778 Aug. 4, 2004.

Chou et al., Ultrafast and Direct Imprint of Nanostructures in Silicon, Nature, col. 417, (Jun. 2002), pp. 835-837 Jun. 1, 2002.

Chou et al., Nanoimprint Lithography, Journal of Vacuum Science Technolgoy B 14(16), pp. 4129-4133 Nov. 1, 1996.

Colburn et al., Development and Advantages of Step-and-Flash Lithography, Solid State Technology Jul. 1, 2001.

Colburn et al., Characterization and Modeling of Volumetric and Mechanical Properties for Step and Flash Imprint Lithography Photopolymers, Journal of Vacuum Science Technology. vol. b. 19(6) Nov. 1, 2001.

Sol-Gel Technology, www.chemat.com/html/solgel.html Jan. 14, 2004.

Sol-Gel Chemistry, www.prsc/usm.edu/mauritz/solgel.html Feb. 2, 2004.

Hakovirta et al., Optical Properties of Fluorinated Diamond-Like Carbon Films Produced by Pulsed Glow Discharge Plasma Immersion Ion Processing, Journal of Applied Physics 88(3); pp. 1456-1459 Aug. 1, 2000.

Yu et al., Properties of Fluorinated Amorphous Diamond Like Carbon Films by PECVD, Applied Surface Science 219 (3-4); pp. 228-237 Dec. 1, 2003.

Compon et al., Electroanalysis at Diamond-Like and Doped-Diamond Electrodes, Electroanalysis 15(17); pp. 1349-1363 Sep. 1, 2003.

Mansano et al., Protective Carbon Layer for Chemical Corrosion of Stainless Steel, Diamond and Related Materials 12 (3-7); pp. 749-752 Mar. 1, 2003.

Butter et al., Production and Wetting Properties of Fluorinated Diamond-Like Carbon Coatings, Thin Solid Films, 311(1-2); pp. 107-113 Dec. 31, 1997.

Hakovirta et al., Heat Resistance of Fluorinated Diamond-Like Carbon Films, Diamond and Related Materials 10(8); pp. 1486-1490 Aug. 1, 2001.

Zhu et al., The Improvement of the Oxidation Resistance of TiAl Alloys by Fluorine Plasma-Based Ion Implantation, Surface and Coatings Technology 158; pp. 502-507 Sep. 1, 2002.

Yao et al., Structural, Mechanical and Hydrophobic Properties of Fluorine-Doped Diamond-Like Carbon Films Synthesized by Plasma Immersion Ion Implantation and Deposition (PIII-D), Applied Surface Science 230; pp. 172-178 Apr. 17, 2004.

Bailey et al., Step and Flash Imprint Lithography: Defect Analysis, Journal of Vacuum Science, B 19(6), pp. 2806-2810 Nov. 1, 2001.

Bailey et al., Step and Flash Imprint Lithography: Template Surface Treatment and Defect Analysis, Journal of Vacuum Science, B 18(6), pp. 3572-3577 Nov. 1, 2000.

Schneider et al., Stripes of Partially Fluorinated Alkyl Chains: Dipolar Langmuir Monolayers, J. Chem. Phys. vol. 122, Issue 9 Mar. 1, 2005.

Data Sheet for MAK (Methyl n-Amyl Ketone), www.sp-chem.com/fine_e Jan. 1, 2003.

Data Sheet for gamma-Glycidoxypropyltrimethoxysilane, www.powerchemical.net/3100.htm Dec. 5, 2003.

Silicon or Silica, www.mii.org/Minerals/photosil Mar. 31, 2005.

Electronic Devices and Circuits, people.deas.harvard.edu/~jones/es154/lectures/lecture_2/materials/materials.html Mar. 31, 2005.

Feynman, There's Plenty of Room at the Bottom, Dec. 1, 1959.

Data Sheet for Cymel 303ULF, www.cytec.com, Jan. 1, 2000.

Data Sheet for Cycat 4040, www.cytec.com, Jan. 1, 1990.

International Chemical Safety Card for p-Toluenseulfonic Acid, www.itcilo.it/english/actrav/telearn/osh/ic/104154.htm Dec. 5, 2003.

Data Sheet for p-Toluenesulfonic Acid, NIOSH Manual of Analytical Methods (NMAM), Fourth Editions, Dec. 5, 2003.

Data Sheet for Dow Corning Z-6018, Jan. 1, 2001.

Data Sheet for Methyl Amyl Ketone, www.arb.ca.gov/db/solvents/solvent_pages/Ketones-HTML/methyl_amyl.htm Mar. 31, 2005.

Golden et al., Designing Porous Low-k Dielectrics, www.reed-electronics.com/semiconductor/index.asp?layout=articlePrint&articleID=CA82824 Apr. 6, 2005.

Padovani et al., Chemically Bonded Porogens in Methylsilsesquioxane: I. Structure and Bonding, Journal of the Electrochemical Society, 149 (12) F161-F170 Oct. 16, 2002.

Wolf et al., Silicon Processing for the VLSI Era, vol. 1—Process Technology, pp. 407-413 Jan. 1, 1986.

Taniguchi et al., Diamond Nanoimprint Lithography, Nanotechnology, 2002, vol. 13, No. 5, pp. 592-596(5) Jan. 1, 2002.

Kiyohara et al., Abstract of Plasma Etching of CVD Diamond Films using an ECR-type Oxygen Source, http://www.iop.org/EJ/abstract/0957-4484/10/4/304 Sep. 26, 2003.

Wolf et al., Silicon Processing for the VLSI Era, vol. 1—Process Technology, pp. 541, 542, 544, 564, 565 Jan. 1, 1986.

Abstract of Japanese Patent 61-040845, Feb. 27, 1986.

Abstract of Japanese Patent 02-248480, Oct. 4, 1990.

Abstract of Japanese Patent 3-090345, Apr. 16, 1991.

Abstract of Japanese Patent 09-278490, Oct. 28, 1997.

Xu et al., Development of Imprint Materials for the Step and Flash Imprint Lithography Process, SPIE Microlithography Conference Feb. 1, 2004.

Data Sheet for Silsequioxanes, Aldrich Website, Sep. 20, 2005.

Dent et al., Microelectronic Grade Silicone Materials for CSP, Dow Corning Corporation Jan. 1, 1999.

Barclay et al., Bilayer Resist Solutions for Sub 100nm Device Production, Shipley Company.

Huang et al., Reversal Imprinting by Transferring Polymer from Mold to Substrate, J. Vac. Sc. Technol. B 20(6); pp. 2872-2876 Nov. 1, 2002.

Translation of Japanese Patent 61-40845, Feb. 1, 1986.

Translation of Japanese Patent 02-248480, Oct. 1, 1990.

Translation of Japanese Patent 03-090345, Apr. 1, 1991.

Translation of Japanese Patent 09-278490, Oct. 1, 1997.

Abstract of Japanese Patent 03-090345, Apr. 1, 1991.

Abstract of Japanese Patent 09-278490, Oct. 1, 1997.

Yoneda et al., Translation of Japanese Patent 02-248480, Transparent Substrate with Water-Repellent and Antistaining Properties, and Structure Equipped Therewith Oct. 4, 1990.

Colburn et al., Dissertation for the Degree of Doctor of Philosophy, Step and Flash Imprint Lithography: A Low-Pressure, Room-Temperature Nanoimprint Lithography Aug. 1, 2001.

DuPont Zonyl Fluorochemical Intermediates, www.dupont.com/zonyl/pdf/intermediates.pdf; pp. 1-16 Jun. 21, 2003.

DuPont Zonyl UR, www.dupont.com/zonyl/pdf/UR.pdf; pp. 1-2 Jun. 21, 2003.

DuPont Zonyl FSN, www.dupont.com/zonyl/odf/FSN.pdf; pp. 1-2 Aug. 24, 2003.

Masurf FS-230, www.masonsurfactants.com/Products/Masurf_FS_230.htm; pp. 1-2 Apr. 5, 2004.

Yoneda et al., Translation of Japanese Patent 02-248480, Transparent Substrate Material with Water-Repllent and Anti-Staining Properties and Structure Equipped with Same Oct. 4, 1990.

FC-4432 Produce Brochure, 3M Fluorosurfactant Mar. 1, 2002.

U.S. Appl. No. 11/508,765, naming Inventors Xu et al., entitled Composition for an Etching Mask Comprising a Silicon-Containing Material, filed Aug. 23, 2006.

Morita et al., Three-Dimensional Nanoimprint Fabrication by Focused-Ion-Beam Chemical Vapor Deposition, Jpn. J. Appl. Phys., vol. 42, Pt. 1, No. 6B, pp. 3874-3876 Jan. 1, 2003.

Dorfman et al., Diamond-like nanocomposites (DLN), Thin Solid Films, vol. 212; pp. 267-273 May 15, 1992.

U.S. Appl. No. 11/560,266, naming Inventors Xu, entitled Methods and Compositions for Providing Preferential Adhesion and Release of Adjacent Surfaces, filed Nov. 15, 2006.

U.S. Appl. No. 11/734,542, naming Inventors Xu et al., entitled Method for Imprint Lithography Utilizing an Adhesion Primer Layer, filed Apr. 12, 2007.

U.S. Appl. No. 11/837,757, naming Inventors Xu et al., entitled Composition to Reduce Adhesion between a Conformable Region and a Mol, filed Aug. 13, 2007.

Abstract of Japanese patent 02-192045, Jul. 27, 1990.

* cited by examiner

METHOD FOR CONTROLLING DISTRIBUTION OF FLUID COMPONENTS ON A BODY

CROSS REFERENCE TO RELATED APPLICATIONS

The present application is a continuation-in-part of U.S. published patent application 2006-0062922-A1, filed as U.S. patent application Ser. No. 10/948,511 on Sep. 23, 2004 entitled "Polymerization Technique to Attenuate Oxygen Inhibition of Solidification of Liquids and Composition Therefor," which is incorporated by reference herein.

BACKGROUND OF THE INVENTION

The field of invention relates generally to nano-fabrication of structures. More particularly, the present invention is directed to methods for controlling distribution of fluid components on a body in imprint lithographic processes.

Nano-scale fabrication involves the fabrication of very small structures, e.g., having features on the order of one nanometer or more. A promising process for use in nano-scale fabrication is known as imprint lithography. Exemplary imprint lithography processes are described in detail in numerous publications, such as United States published patent application 2004/0065976 filed as U.S. patent application Ser. No. 10/264,960, entitled "Method and a Mold to Arrange Features on a Substrate to Replicate Features having Minimal Dimensional Variability"; United States published patent application 2004/0065252 filed as U.S. patent application Ser. No. 10/264,926, entitled "Method of Forming a Layer on a Substrate to Facilitate Fabrication of Metrology Standards"; and U.S. Pat. No. 6,936,194, issued Aug. 30, 2005 and entitled "Functional Patterning Material For Imprint Lithography Processes," all of which are assigned to the assignee of the present invention.

Figure 1:
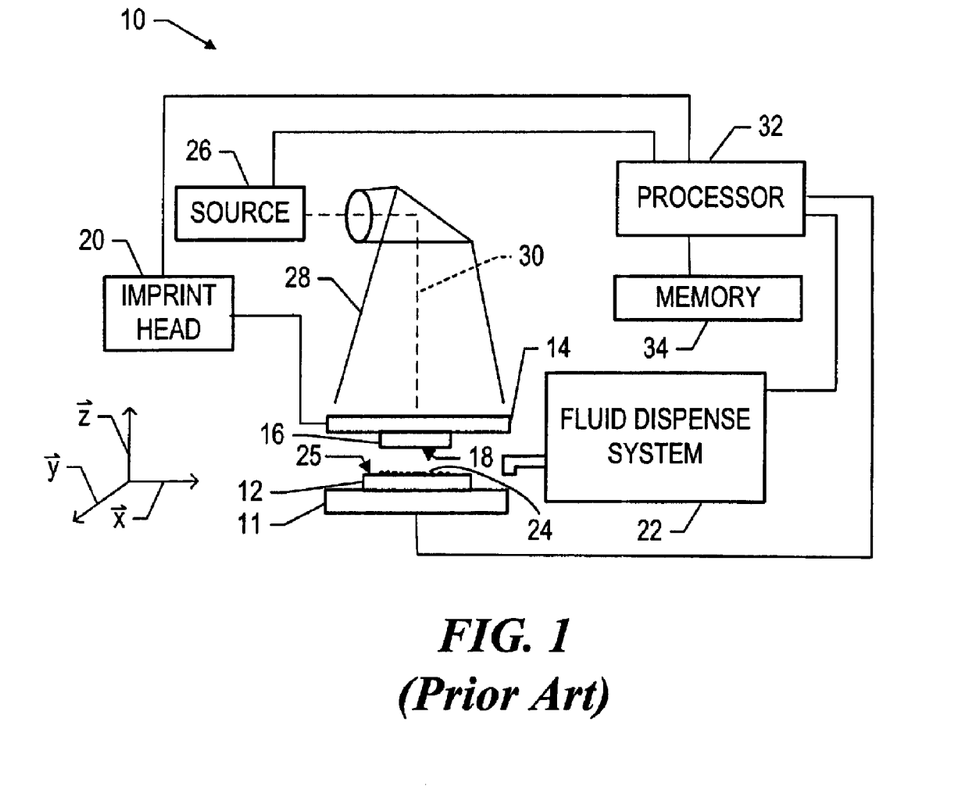
FIG. 1 is a simplified plan view of a lithographic system in accordance with the prior art.

Referring to FIG. 1, the basic concept behind imprint lithography is forming a relief pattern on a substrate that may function as, inter alia, an etching mask so that a pattern may be formed into the substrate that corresponds to the relief pattern. A system 10 employed to form the relief pattern includes a stage 11 upon which a substrate 12 is supported, and a template 14 having a mold 16 with a patterning surface 18 thereon. Patterning surface 18 may be substantially smooth and/or planar, or may be patterned so that one or more recesses are formed therein. Template 14 is coupled to an imprint head 20 to facilitate movement of template 14. A fluid dispense system 22 is coupled to be selectively placed in fluid communication with substrate 12 so as to deposit polymerizable material 24 thereon. A source 26 of energy 28 is coupled to direct energy 28 along a path 30. Imprint head 20 and stage 11 are configured to arrange mold 16 and substrate 12, respectively, to be in superimposition, and disposed in path 30. Either imprint head 20, stage 11, or both vary a distance between mold 16 and substrate 12 to define a desired volume therebetween that is filled by polymerizable material 24.

Typically, polymerizable material 24 is disposed upon substrate 12 before the desired volume is defined between mold 16 and substrate 12. However, polymerizable material 24 may fill the volume after the desired volume has been obtained. After the desired volume is filled with polymerizable material 24, source 26 produces energy 28, which causes polymerizable material 24 to solidify and/or cross-link, forming polymeric material conforming to the shape of the substrate surface 25 and mold surface 18. Control of this process is regulated by processor 32 that is in data communication with stage 11 imprint head 20, fluid dispense system 22, and source 26, operating on a computer-readable program stored in memory 34.

An important characteristic with accurately forming the pattern in the polymerizable material is to reduce, if not prevent, adhesion to the mold of the polymeric material, while ensuring suitable adhesion to the substrate. This is referred to as preferential release and adhesion properties. In this manner, the pattern recorded in the polymeric material is not distorted during separation of the mold. Prior art attempts to improve the release characteristics employ a release layer on the surface of the mold. The release layer is typically hydrophobic and/or has low surface energy. The release layer adheres to the mold by covalent chemical bonding. Providing the release layer improves release characteristics. This is seen by minimization of distortions in the pattern recorded into the polymeric material that are attributable to mold separation. This type of release layer is referred to, for purposes of the present discussion, as an a priori release layer, i.e., a release layer that is solidified to the mold.

Another prior art attempt to improve release properties is described by Bender et al. in "Multiple Imprinting in UV-based Nanoimprint Lithography: Related Material Issues," Microeletronic Engineering 61-62 (2002), pp. 407-413. Specifically, Bender et al. employ a mold having an a priori release layer in conjunction with a fluorine-treated UV curable material. To that end, a UV curable layer is applied to a substrate by spin-coating a 110 cPs UV curable fluid to form a UV curable layer. The UV curable layer is enriched with fluorine groups to improve the release properties.

A need exists, therefore, to improve the preferential release and adhesion properties of a mold employed in imprint lithography processes.

SUMMARY OF THE INVENTION

The present invention provides a method of controlling the distribution of a fluid on a body that features compensating for varying distribution of constituent components of a composition that move over a surface of a substrate. Specifically, the quantity of a surfactant component of a composition varied over the surface upon which the composition was spread to form a contiguous layer. Typically, the composition is deposited upon the surface as a plurality of spaced-apart droplets. It was discovered that the air-liquid interface of each droplet varied in dimension as the same was spread over the surface. This resulted in there being a depletion of surfactants, referred to as surfactant depletion regions (SDR) in the area of the contiguous layer proximate to the situs of the droplets and a surfactant rich region (SRR) in area of the layer located proximate to spaces between the droplets. This is believed to increase the probability that pitting of a solidified layer formed from the contiguous layer occurs. The pitting is believed to be attributable to, inter alia, from an uneven distribution of surfactant on the mold. A lamella layer is generated on the mold after each imprint. The lamella layer is formed primarily from surfactants present in the material disposed between the mold and the substrate during imprinting. An uneven distribution of surfactants in this material causes an uneven distribution of surfactants in the lamella layer. This in turn exacerbates the differences in surfactant quantities in the SDR and SRR as the number of imprints increases. To compensate for the varying distribution of surfactants in a given layer, the method includes generating a sequence of patterns of liquid upon a substrate, each of which includes a plurality of spaced-apart liquid regions, with interstices being defined between adjacent liquid regions. A second of the patterns of liquid of the sequence is arranged so that the liquid regions associated therewith are in superimposition with the interstices of a first of the patterns of liquid of the sequence. These and other embodiments are described below.

DETAILED DESCRIPTION OF THE INVENTION

Figure 2:
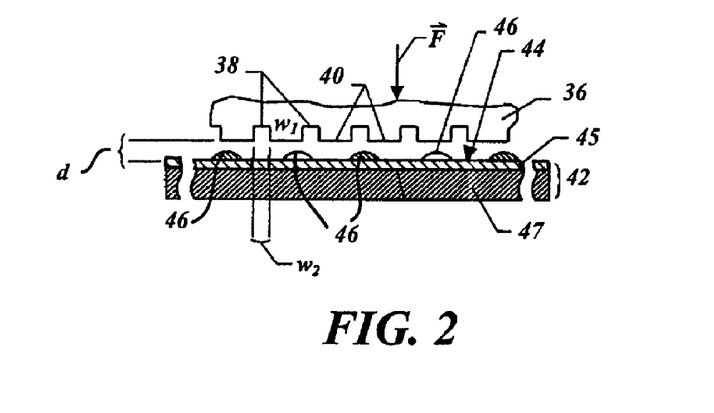
FIG. 2 is a simplified elevation view of a template and imprinting material disposed on a substrate in accordance with the present invention.

Referring to FIGS. 1 and 2, a mold 36, in accordance with the present invention, may be employed in system 10, and may define a surface having a substantially smooth or planar profile (not shown). Alternatively, mold 36 may include features defined by a plurality of spaced-apart recessions 38 and protrusions 40. The plurality of features defines an original pattern that forms the basis of a pattern to be formed on a substrate 42. Substrate 42 may comprise a bare wafer or a wafer with one or more layers disposed thereon, one of which is shown as primer layer 45. To that end, reduced is a distance "d" between mold 36 and substrate 42. In this manner, the features on mold 36 may be imprinted into a conformable region of substrate 42, such as an imprinting material disposed on a portion of surface 44 that presents a substantially planar profile. It should be understood that the imprinting material may be deposited using any known technique, e.g., spin-coating, dip coating and the like. In the present example, however, the imprinting material is deposited as a plurality of spaced-apart discrete droplets 46 on substrate 42.

Figure 3:
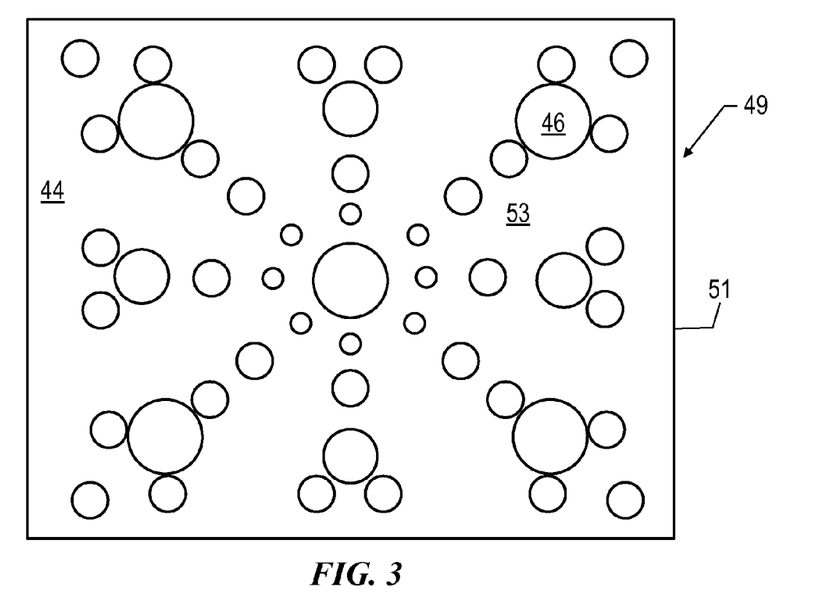
FIG. 3 is a top down view of a region of the substrate, shown in FIG. 2, upon which patterning occurs employing a pattern of droplets of polymerizable fluid disposed thereon.
Figure 4:
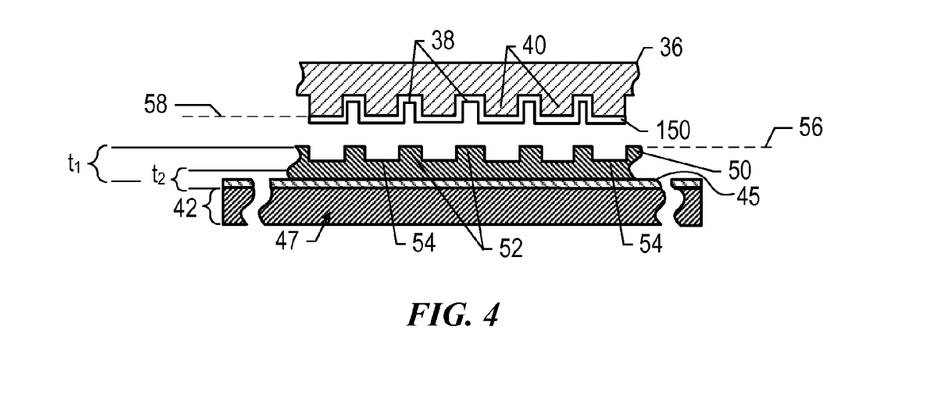
FIG. 4 is a simplified elevation view of an imprint device spaced-apart from the patterned imprinting layer, shown in FIG. 1, after patterning in accordance with the present invention.

Referring to both FIGS. 3 and 4, droplets 46 are arranged in a pattern 49 to facilitate formation of a contiguous layer 50. Imprinting material is formed from a composition that may be selectively polymerized and cross-linked to record the original pattern therein, defining a recorded pattern. Specifically, the pattern recorded in the imprinting material is produced, in part, by interaction with mold 36, e.g., electrical interaction, magnetic interaction, thermal interaction, mechanical interaction or the like. In the present example, mold 36 is spaced-apart from substrate 42 with the area of surface 44 in superimposition therewith being shown by periphery 51. Portions of surface 44 not covered by droplets 46 and within periphery 51 define voids 53. Regions of mold 36 in superimposition with droplets 46 define deposition zones. It should be understood that for purposes of the present example, each side of periphery 51 is 25 millimeters in length, i.e., the area encompassed by periphery is 25×25 mm square. Droplets 46 are shown to reflect an accurate depiction of proportional size a diameter thereof compared to the length of one side of periphery 51. Although droplets 46 are shown being different sizes, the present invention envisions an embodiment wherein all the droplets 46 are of the same size, i.e., contain the same quantity of liquid. Regions of mold 36 in superimposition with voids 53 define interstices. Mold 36 comes into mechanical contact with the imprinting material, spreading droplets 46, so as to generate a contiguous layer 50 of the imprinting material over surface 44. In one embodiment, distance "d" is reduced to allow sub-portions 52 of imprinting material to ingress into and fill recessions 38. To facilitate filling of recessions 38, before contact between mold 36 and droplets 46, the atmosphere between mold 36 and droplets 46 is saturated with helium or is completely evacuated or is a partially evacuated atmosphere of helium. It may be desired to purge the volume, defined between mold 36, surface and droplets 46, shown in FIG. 2, for example with Helium gas flowed at 5 pounds per square inch (psi), before contact occurs. An exemplary purging technique is disclosed in U.S. Pat. No. 7,090,716 issued Aug. 15, 2006, entitled SINGLE PHASE FLUID IMPRINT LITHOGRAPHY, which is incorporated by reference herein.

The imprinting material is provided with the requisite properties to completely fill recessions 38 while covering surface 44 with a contiguous formation of the imprinting material. In the present embodiment, sub-portions 54 of imprinting material in superimposition with protrusions 40 remain after the desired, usually minimum, distance "d" has been reached. This action provides contiguous layer 50 with sub-portions 52 having a thickness $t_1$, and sub-portions 54, having a thickness $t_2$. Thicknesses "$t_1$," and "$t_2$," may be any thickness desired, dependent upon the application. Thereafter, contiguous layer 50 is solidified by exposing the same to the appropriate curing agent, e.g., actinic energy, such as broadband ultra violet energy, thermal energy or the like, depending upon the imprinting material. This causes the imprinting material to polymerize and cross-link. The entire process may occur at ambient temperatures and pressures, or in an environmentally-controlled chamber with desired temperatures and pressures. In this manner, contiguous layer 50 is solidified to provide side 56 thereof with a shape conforming to a shape of a surface 58 of mold 36.

Referring to FIGS. 1, 2 and 3, the characteristics of the imprinting material are important to efficiently pattern substrate 42 in light of the unique patterning process employed. For example, it is desired that the imprinting material have certain characteristics to facilitate rapid and even filling of the features of mold 36 so that all thicknesses $t_1$ are substantially uniform and all thicknesses $t_2$ are substantially uniform. To that end, it is desirable that the viscosity of the imprinting material be established, based upon the deposition process employed, to achieve the aforementioned characteristics. As mentioned above, the imprinting material may be deposited on substrate 42 employing various techniques. Were the imprinting material deposited as a plurality of discrete and spaced-apart droplets 46, it would be desirable that a composition from which the imprinting material is formed have relatively low viscosity, e.g., in a range of 0.5 to 30 centipoises (cPs).

Considering that the imprinting material is spread and patterned concurrently, with the pattern being subsequently solidified into contiguous layer 50 by exposure to radiation, it would be desired to have the composition wet surface of substrate 42 and/or mold 36 and to avoid subsequent pit or hole formation after polymerization. Were the imprinting material deposited employing spin-coating techniques, it would be desired to use higher viscosity materials, e.g., having a viscosity greater than 10 cPs and typically, several hundred to several thousand cPs, with the viscosity measurement being determined in the absence of a solvent. The total volume contained in droplets 46 may be such so as to minimize, or avoid, a quantity of the imprinting material from extending beyond the region of surface 44 in superimposition with mold 36, while obtaining desired thicknesses $t_1$ and $t_2$, e.g., through capillary attraction of the imprinting material with mold 36 and surface 44 and surface adhesion of the imprinting material.

In addition to the aforementioned characteristics, referred to as liquid phase characteristics, it is desirable that the composition provides the imprinting material with certain solidified phase characteristics. For example, after solidification of contiguous layer 50, it is desirable that preferential adhesion and release characteristics be demonstrated by the imprinting material. Specifically, it is beneficial for the composition from which the imprinting material is fabricated to provide contiguous layer 50 with preferential adhesion to substrate 42 and preferential release of mold 36. In this fashion, reduced is the probability of distortions in the recorded pattern resulting from the separation of mold 36 therefrom due to, inter alia, tearing, stretching or other structural degradation of contiguous layer 50.

Figure 5:
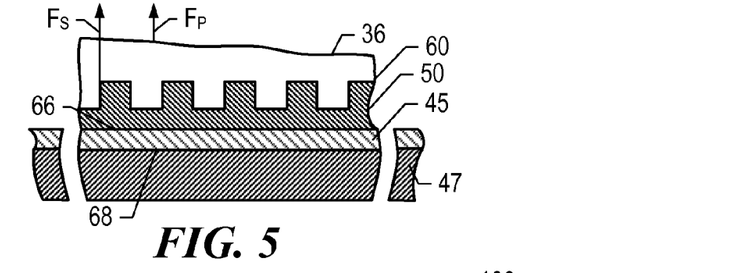
FIG. 5 is a detailed view of the template, shown in FIG. 2 being removed after solidification of imprinting material in accordance with a second embodiment of the present invention.

For example, with reference to FIGS. 4 and 5, upon separation of mold 36, contiguous layer 50 is subjected to a separation force Fs. Separation force Fs is attributable to a pulling force $F_P$ on mold 36 and adhering forces, e.g., Van der Waals forces, between contiguous layer 50 and mold 36. Pulling force $F_P$ is used to break vacuum seal. It is desired to decouple mold 36 from contiguous layer 50 without unduly distorting contiguous layer 50. One manner in which to control distortion of contiguous layer 50 during separation of mold 36 therefrom is by providing the composition from which the imprinting material is formed with releasing agents, such as surfactants.

The constituent components of the composition that form the imprinting material and layer 45 to provide the aforementioned characteristics may differ. This results from substrate 42 being formed from a number of different materials, i.e. providing differing magnitudes of adhering forces $F_A$. As a result, the chemical composition of surface 44 varies dependent upon the material from which substrate 42 is formed. For example, substrate 42 may be formed from silicon, plastics, gallium arsenide, mercury telluride, and composites thereof. As mentioned above, substrate 42 may include one or more layers shown as primer layer 45, e.g., dielectric layer, metal layer, semiconductor layer, planarization layer and the like, upon which contiguous layer 50 is generated. To that end, primer layer 45 would be deposited upon a wafer 47 employing any suitable technique, such as chemical vapor deposition, spin-coating and the like. Additionally, primer layer 45 may be formed from any suitable material, such as silicon, germanium and the like. Additionally, mold 36 may be formed from several materials, e.g., fused-silica, quartz, indium tin oxide diamond-like carbon, MoSi, sol-gels and the like.

An exemplary composition that may be employed from which to form contiguous layer 50 is as follows:

Composition isobornyl acrylate
n-hexyl acrylate
ethylene glycol diacrylate
2-hydroxy-2-methyl-1-phenyl-propan-1-one
$R_1R_2$ An acrylate component of the bulk material, isobornyl acrylate (IBOA), has the following structure:

and comprises approximately 47% of COMPOSITION by weight, but may be present in a range of 20% to 80%, inclusive. As a result, the mechanical properties of solidified imprinting layer 134 are primarily attributable to IBOA. An exemplary source for IBOA is Sartomer Company, Inc. of Exton, Pa. available under the product designation SR 506.

The component n-hexyl acrylate (n-HA) has the following structure:

and comprises approximately 25% of bulk material by weight, but may be present in a range of 0% to 40%, inclusive. Also providing flexibility to formation 50, n-HA is employed to reduce the viscosity of the prior art bulk material so that bulk material, in the liquid phase, has a viscosity in a range 2-9 Centipoises, inclusive. An exemplary source for the n-HA component is the Aldrich Chemical Company of Milwaukee, Wis.

A cross-linking component, ethylene glycol diacrylate, has the following structure:

and comprises approximately 15% of bulk material by weight, and may be present in a range of 10% to 50%, inclusive. EGDA also contributes to the modulus and stiffness buildup, as well as facilitates cross-linking of n-HA and IBOA during polymerization of the bulk material.

An initiator component, 2-hydroxy-2-methyl-1-phenyl-propan-1-one, is available from Ciba Specialty Chemicals of Tarrytown, N.Y. under the trade name DAROCUR® 1173, and has the following structure:

and comprises approximately 3% of the bulk material by weight, and may be present in a range of 1% to 5%, inclusive. The initiator is responsive to a broad band of ultra-violet radiation generated by a medium-pressure mercury lamp. In this manner, the initiator facilitates cross-linking and polymerization of the components of the bulk material. The constituent components of COMPOSITION, IBOA, n-HA, EGDA and 2-hydroxy-2-methyl-1-phenyl-propan-1-one form the bulk material of the same.

A surfactant component, $R_1R_2$, is a non-ionic surfactant sold by Mason Chemical Company of Arlington Heights, Ill. under the product names MASURF® FS-2000. The surfactant component consists of approximately 2%, by weight, of the bulk material and acts as a release agent of COMPOSITION by facilitating preferential adhesion and release of contiguous layer 50, once solidified.

The advantages of this patterning process are manifold. For example, the thickness differential between protrusions 40 and recessions 38 facilitates formation, in substrate 42, of a pattern corresponding to the recorded pattern formed in contiguous layer 50. Specifically, the thickness differential between $t_1$ and $t_2$ of protrusions 40 and recession 38, respectively, results in a greater amount of etch time being required before exposing regions of substrate 42 in superimposition with protrusions 40 compared with the time required for regions of substrate 42 in superimposition with recession 52 being exposed. For a given etching process, therefore, etching will commence sooner in regions of substrate 42 in superimposition with recessions 38 than regions in superimposition with protrusions 40. This facilitates formation of a pattern in substrate corresponding to the aforementioned recorded pattern. By properly selecting the imprinting materials and etch chemistries, the relational dimensions between the differing features of the pattern eventually transferred into substrate 42 may be controlled as desired. To that end, it is desired that the etch characteristics of the recorded pattern, for a given etch chemistry, be substantially uniform.

As a result, the characteristics of the imprinting material are important to efficiently pattern substrate 42 in light of the unique patterning process employed. As mentioned above, the imprinting material is deposited on substrate 42 as a plurality of discrete and spaced-apart droplets 46. The combined volume of droplets 46 is such that the imprinting material is distributed appropriately over an area of surface 44 where the recorded pattern is to be formed. In this fashion, the total volume of the imprinting material in droplets 46 defines the distance "d", to be obtained so that the total volume occupied by the imprinting material in the gap defined between mold 36 and the portion of substrate 42 in superimposition therewith once the desired distance "d" is reached is substantially equal to the total volume of the imprinting material in droplets 46. To facilitate the deposition process, it is desired that the imprinting material provide rapid and even spreading of the imprinting material in droplets 46 over surface 44 so that all thicknesses $t_1$ are substantially uniform and all residual thicknesses $t_2$ are substantially uniform.

Figure 6:
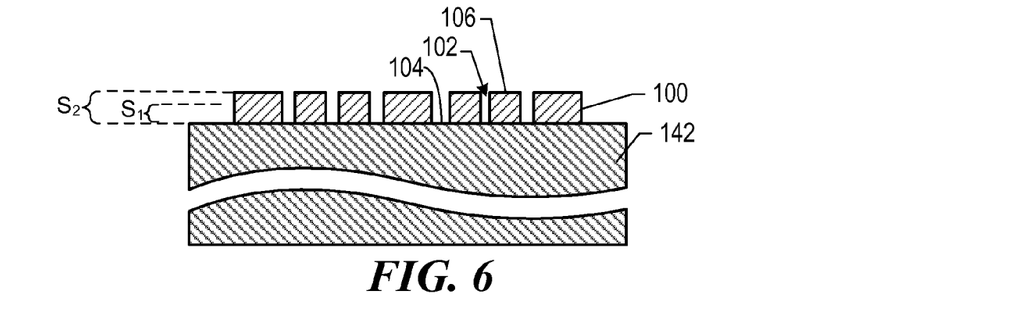
FIG. 6 is a cross-sectional view of an imprinted layer showing varying thickness that the present invention is directed to reduce if not avoid.

Referring to FIGS. 3 and 6, a problem recognized by the present invention involves varying characteristics of a contiguous layer of imprinting material. Specifically, formed on a substrate 142 was a layer 100 in the manner discussed above, i.e., except with a non-patterned mold (not shown) having a smooth surface, to spread droplets 46. After spreading of droplets 46 the imprinting material was exposed for approximately 700 ms to actinic energy having a wavelength of approximate 365 nm a flux of 77 mW/cm$^2$ to solidify the same. After sequentially forming and solidifying several layers 100 employing mold 36, observed were pits 102 over the area of layers 100 formed later in the sequence. Pits 102 were found to be a complete absence of layer 100 in superimposition with portions 104 of substrate 142 and located between portions 106 of layer 100 having a desired thickness. It is believed that pits 102 result from an uneven surfactant distribution over layer 100 that prevents the bulk material of COMPOSITION from being in superimposition with regions 104. The difference becomes more pronounced as the number of layers 100 imprinted.

Referring to FIGS. 3, 4 and 6, the present invention overcomes these drawbacks by changing the position of droplets 46 in pattern 49 on sequential formation of contiguous layers, such as contiguous layer 50 or 100. The present discussion concerns contiguous layer 100, with the understanding that the same applies to contiguous layer 50, as well. Specifically, it was found that the quantity of the surfactant component of COMPOSITION varied in contiguous layer 100 over the surface upon which the composition was spread to form solidified contiguous layer 100. Typically, the composition is deposited upon surface 44 as a plurality of spaced-apart droplets 46. It was discovered that the surfactant concentration in the air-liquid interface of each droplet varied as the droplet was spread over the surface. This resulted from several factors, including the viscosity differential between the surfactant component of COMPOSITION and the bulk material component of the same and the consumption of the surfactant component by clinging to the mold 36 surface in contact with the COMPOSITION. The presented as surfactant depletion regions (SDR) in the area of the contiguous layer proximate to the situs of the droplets 46, regions 106, and a surfactant rich region (SRR) in areas of the layer located proximate to spaces between the droplets, regions 104.

Figure 7:
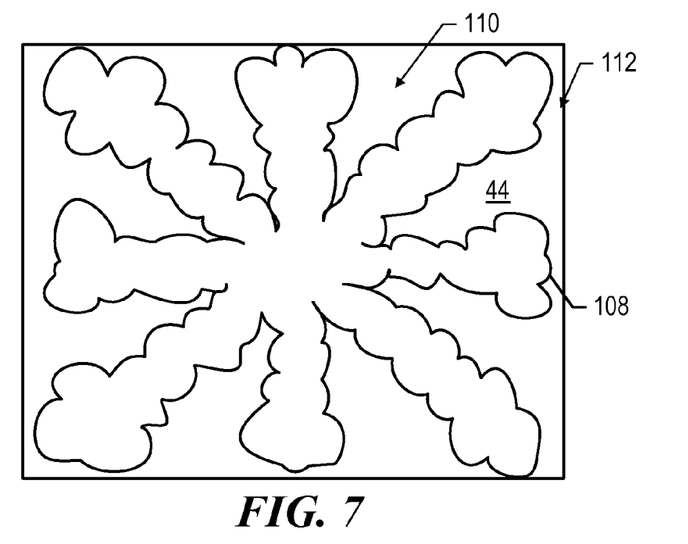
FIG. 7 is a top down view of a region of the substrate, shown in FIG. 2, showing an intermediate pattern formed by the droplets of polymerizable fluid shown in FIG. 3, during spreading.
Figure 8:
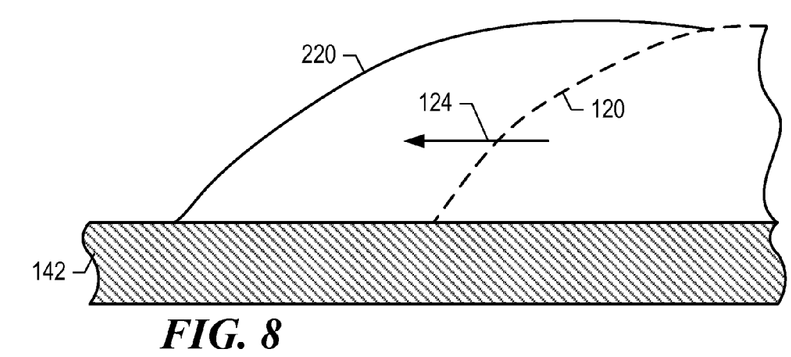
FIG. 8 is a detailed cross-sectional view of a portion of one droplet of imprinting material showing the change in shape of the same during formation of intermediate pattern in accordance with the present invention.
Figure 9:
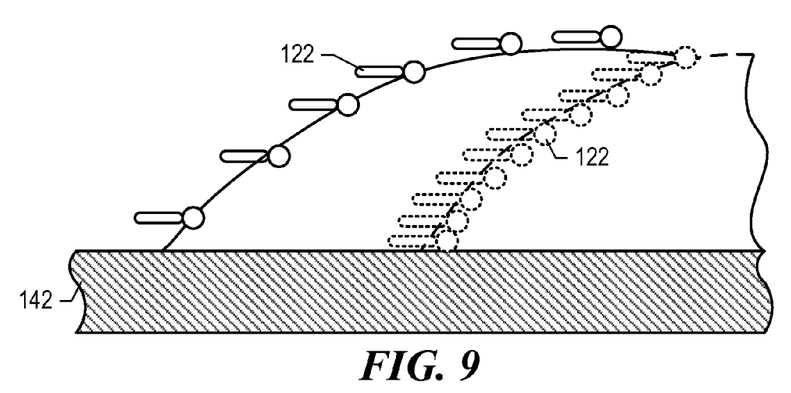
FIG. 9 is a detailed cross-sectional view of a portion of one droplet of imprinting material showing the change is surfactant molecule distribution as the shape of the same changes during formation of intermediate patterns.

Referring to FIGS. 3, 8 and 9, observing that surfactants have an affinity for the region of a liquid proximate to a liquid-air interface it was realized that during formation of a contiguous layer, surfactant molecules underwent redistribution due to the varying size of the liquid-air-interface. Upon deposition of droplets 46 on surface 44, each of the droplets 46 generates an initial liquid-air interface 120. Surfactant molecules 122 are packed tightly, after a predetermined time, at interface 120. As mold 36 interacts with droplets 46, liquid in droplets 46 moves with respect to substrate 42, in direction of the movement shown by arrow 124 forming a series of intermediate patterns, such as pattern 110, before droplets 46 merge to form contiguous layer 100. As droplets 46 move the air-liquid interface 120 moves, shown by liquid-air interface 220, which finally becomes ambient-air interface 108, shown in FIG. 7. This results in the spacing between adjacent surfactant molecules 122 increasing, shown in FIG. 9, for the reasons discussed above. As a result, a greater number of surfactant molecules travel from regions of liquids in superimposition with deposition zones of mold 36, creating SDR regions thereat, and an SRR region in areas of liquid in superimposition with interstices of mold 36, shown in FIG. 4.

Referring to FIGS. 4, 6, 8 and 9, the presence of surfactant molecules 122 in contiguous layer 100 generates a lamella layer 150 on mold 36 after formation of each contiguous layer 100. Lamella layer 150 comprises a densely packed fluid composition of surfactant molecules 122. The distribution of surfactant molecules 122 in lamella layer 150 matches the distribution of surfactant molecules in contiguous layer 100, i.e. SDR regions 102 and SRR region 104. Thus, there is an uneven distribution of surfactant molecules 122 in lamella layer 150. On formation of subsequent contiguous layers, the difference in surfactant molecule distribution in lamella layer 150 may become exacerbated, resulting in an increasing probability that voids may be present in contiguous layer 100. To reduce, if not avoid an uneven distribution of surfactant molecules 122 in layers 100 and 150, a subsequent layer formed by mold 36 would be generated by locating deposition zones of the same to be in superimposition with interstices of a previously formed contiguous layer 100 that includes regions 104, shown more clearly in FIG. 10.

Referring again to FIGS. 4, 6, 8 and 9, in this manner, the existing surfactant molecule 122 distribution present in lamella 150 may be compensated for, at least in part, by the resulting surfactant molecule 122 distribution from spreading of droplets 46 to form contiguous layer 100. This is referred to as a droplet pattern shift in which sequential contiguous layers formed from COMPOSITION is generated by shifting the droplets in the pattern for one of the contiguous layers in the sequence compared to the position of the droplets in the pattern employed to form the previous contiguous layer in the sequence.

Figure 10:
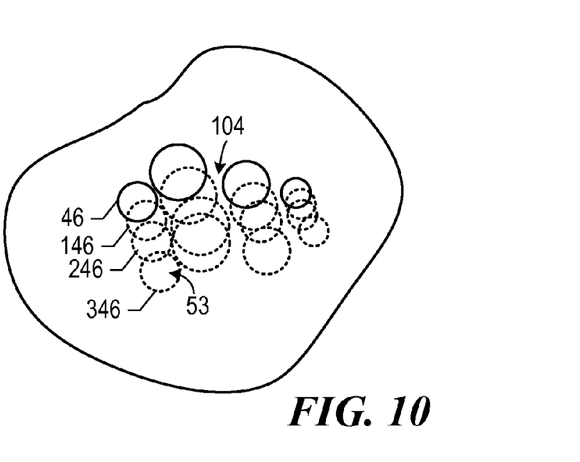
FIG. 10 is a partial top down view of FIG. 3 showing a sequence of droplets deposited on a surface in furtherance of forming a sequence of contiguous layers of imprinting material in accordance with one embodiment of the present invention.

Referring to FIG. 10, it should be understood, however, that it need not be necessary to shift the pattern 49 of droplets so that the entire area of droplets 46 are in superimposition with the interstices. Rather, it is within the spirit of the present invention that there may be an overlap between droplets 46 of one pattern and droplets 146 of the next pattern formed in a sequence. This may be repeated until a pattern is formed corresponding to a subsequent contiguous layer the area of which is entirely within a void 53 of an initial pattern and, therefore, the interstice. Moreover, it may be desirable to vary the quantity of surfactants in one or more of droplets 46, 146, 246 and 346 to avoid pitting of contiguous layer 100, shown in FIG. 6.

The embodiments of the present invention described above are exemplary. Many changes and modifications may be made to the disclosure recited above while remaining within the scope of the invention. The scope of the invention should not, therefore, be limited by the above description, but instead should be determined with reference to the appended claims along with their full scope of equivalents.

What is claimed is:

1. A method of controlling the distribution of fluid components on a body in superimposition with a substrate, the method comprising:
   sequentially contacting the body with a series of patterns of liquid formed on one or more substrates, each pattern in the series comprising a plurality of spaced-apart liquid regions with voids defined between adjacent spaced-apart liquid regions, wherein an arrangement of the plurality of spaced-apart liquid regions in the first pattern of the series differs from an arrangement of the plurality of spaced-apart liquid regions in the second pattern of the series, such that regions of the body that initially contact the spaced-apart liquid regions in the first pattern do not initially contact the spaced-apart liquid regions in the second pattern.

2. A method of controlling the distribution of fluid components on a body in superimposition with a substrate, the method comprising:
   sequentially contacting the body with a series of patterns of liquid formed on one or more substrates, each pattern in the series comprising a plurality of spaced-apart liquid regions with voids defined between adjacent spaced-apart liquid regions, wherein an arrangement of the plurality of spaced-apart liquid regions in the first pattern of the series differs from an arrangement of the plurality of spaced-apart liquid regions in the second pattern of the series, such that regions of the body that initially contact the spaced-apart liquid regions in the first pattern initially partially contacts at least one of the spaced-apart liquid regions in the second pattern.

3. A method of controlling the distribution of fluid components on a body in superimposition with a substrate, the method comprising:
   sequentially contacting the body with a series of patterns of liquid formed on one or more substrates, each pattern in the series comprising a plurality of spaced-apart liquid regions with voids defined between adjacent spaced-apart liquid regions, wherein an arrangement of the plurality of spaced-apart liquid regions in the first pattern of the series differs from an arrangement of the plurality of spaced-apart liquid regions in the second pattern of the series, wherein the spaced-apart liquid regions are droplets of a polymerizable liquid, and wherein sequentially contacting the body with the series of patterns of liquid formed on the one or more substrates comprises:
   depositing a pattern of a first polymerizable liquid comprising a first surfactant upon a first substrate of the one or more substrates to form the first pattern in the series of patterns, the first pattern comprising a first plurality of spaced-apart droplets at first droplet locations, with first voids defined at first void locations between adjacent spaced-apart droplets of the first plurality of droplets;
   contacting the body with the first plurality of spaced-apart droplets to spread the spaced-apart droplets to form a first contiguous layer of the first polymerizable liquid on the first substrate, the first contiguous layer comprising surfactant depletion regions proximate the first droplet locations and surfactant rich regions proximate the first void locations;
   forming a first lamella layer upon the body, wherein the first lamella layer has surfactant rich regions corresponding to the surfactant rich regions of the first contiguous layer and surfactant depletion regions corresponding to the surfactant depletion regions of the first contiguous layer;
   solidifying the first polymerizable liquid to form a solidified layer on the first substrate;
   separating the body with the first lamella layer from the solidified layer;
   depositing a pattern of a second polymerizable liquid comprising a second surfactant upon the first one or another one of the one or more substrates to form the second pattern in the series of patterns, the second pattern comprising a second plurality of spaced-apart droplets at second droplet locations; and
   contacting the body with the second plurality of spaced-apart droplets, wherein at least some of the second droplet locations are in superimposition with at least some of the first surfactant rich regions of the first lamella layer of the body.

4. The method as recited in claim 3 wherein a sub-portion of the second plurality of spaced-apart droplets is partially in superimposition with the surfactant depletion regions of the first lamella layer of the body.

5. The method as recited in claim 3 wherein the droplets of the first plurality of droplets have a first quantity of liquid and the droplets of the second plurality of droplets have a second quantity of liquid, wherein the second quantity of liquid differs from the first quantity of liquid.

6. The method as recited in claim 3 wherein the droplets of the first plurality of droplets have a first quantity of the first surfactant and the droplets of the second plurality of droplets have a second quantity of the second surfactant, wherein the second quantity of the second surfactant differs from the first quantity of the first surfactant.

7. The method as recited in claim 3 wherein the droplets of the first plurality of droplets have a first quantity of the first surfactant and the droplets of the second plurality of droplets have a second quantity of the second surfactant, wherein the second quantity of the second surfactant is the same as said first quantity of the first surfactant.

8. A method of controlling the distribution of fluid components on a body, the method comprising:
depositing a first plurality of spaced-apart droplets of a first polymerizable liquid comprising a first surfactant upon a substrate;
aligning the body and the substrate, with portions of the body in superimposition with the droplets defining first deposition zones and portions of the body between said first deposition zones defining first interstices;
contacting the body with the first plurality of spaced-apart droplets to form a contiguous layer of the polymerizable liquid between the body and the substrate and to form surfactant depletion regions and surfactant rich regions on the body;
solidifying the contiguous layer to form a solidified layer;
separating the body from the solidified layer;
forming a second plurality of spaced-apart droplets of a second polymerizable liquid comprising a second surfactant upon the same or an additional substrate; and
aligning the body and the same or the additional substrate, with portions of the body in superimposition with the droplets of the second plurality of droplets defining second deposition zones and portions of the body between the second deposition zones defining second interstices, wherein the second plurality of spaced-apart droplets is arranged with the second deposition zones in superimposition with the first interstices and the second interstices in superimposition with the first deposition zones.

9. The method as recited in claim 8 wherein solidifying comprises exposing the contiguous layer to actinic energy, and wherein the surfactant rich regions of the body are in superimposition with the second deposition zones and the surfactant depletion regions of the body are in superimposition with the second interstices.

10. The method as recited in claim 8 wherein forming the second plurality of droplets comprises forming each of the droplets of the second plurality of droplets with an area such that each of the droplets is completely in superimposition with one of the first interstices.

11. The method as recited in claim 8 wherein forming the second plurality of droplets comprises forming each of the droplets such that a sub-portion of each of the droplets of the second plurality of droplets is in superimposition with one of the first deposition zones.

12. The method as recited in claim 8 wherein depositing the first plurality of spaced-apart droplets comprises providing each of the droplets of the first plurality with a first quantity of liquid and forming the second plurality of droplets comprises providing each of the droplets of the second plurality of droplets with a second quantity of liquid, wherein the second quantity of liquid differs from the first quantity of liquid.

13. The method as recited in claim 8 wherein depositing the first plurality of spaced-apart droplets comprises providing each of the droplets of the first plurality of droplets with a first quantity of the first surfactant and forming the second plurality of droplets comprises providing the droplets of the second plurality of droplets with a second quantity of the second surfactant, wherein the second quantity of the second surfactant differs from the first quantity of the first surfactant.

14. The method as recited in claim 8 wherein depositing the first plurality of spaced-apart droplets comprises forming the droplets of the first plurality of droplets to have a first quantity of the first surfactant and forming the second plurality of droplets comprises forming the droplets of the second plurality of droplets to have a second quantity of the second surfactant, wherein the second quantity of the second surfactant is the same as the first quantity of the first surfactant.

15. A method of controlling the distribution of fluid components on a body in superimposition with a substrate, the method comprising:
depositing a first plurality of spaced-apart droplets of a polymerizable liquid comprising a first surfactant upon the substrate, with regions of the body in superimposition with the droplets defining first deposition zones and regions of the body between the first deposition zones defining first interstices;
contacting the first plurality of spaced-apart droplets with the body;
spreading the droplets of the first plurality of spaced-apart droplets to form a first contiguous layer of the liquid between the body and the substrate;
exposing the first contiguous layer of the polymerizable liquid to actinic energy to form a first solidified layer, wherein the first solidified layer comprises surfactant rich regions in superimposition with the first interstices and surfactant depletion regions in superimposition with the first deposition zones;
separating the body from the first solidified layer;
forming a second plurality of spaced-apart droplets of a second polymerizable liquid comprising a second surfactant upon the first solidified layer, with portions of the body in superimposition with the droplets of the second plurality defining second deposition zones and portions of the body between the second deposition zones defining second interstices, wherein the second plurality of spaced-apart droplets is arranged with the second deposition zones in superimposition with the surfactant rich regions of the first solidified layer and the second interstices in superimposition with the surfactant depletion regions of the first solidified layer;
contacting the second plurality of spaced-apart droplets with the body;
spreading the droplets of the second plurality of spaced-apart droplets to form an additional contiguous layer of the liquid between the body and the first solidified layer; and
exposing the additional contiguous layer of the liquid to actinic energy to form an additional solidified layer on the first solidified layer.

16. The method as recited in claim 15 wherein forming the second plurality of spaced-apart droplets comprises providing each of the droplets of the second plurality of droplets with an area to completely cover one of the first interstices.

17. The method as recited in claim 15 wherein forming the second plurality of spaced-apart droplets comprises providing each of the droplets of the second plurality of droplets with an area, a sub-portion of which is in superimposition with one of the first deposition zones.

18. The method as recited in claim 15 wherein depositing the first plurality of spaced-apart droplets comprises providing each of the droplets of the first plurality with a first quantity of liquid and forming the second plurality of spaced-apart droplets comprises providing each of the droplets of the second plurality of droplets with a second quantity of liquid, wherein the second quantity of liquid differs from the first quantity of liquid.

19. The method as recited in claim 15 wherein depositing the first plurality of spaced-apart droplets comprises providing each of the droplets of the first plurality of droplets with a first quantity of the first surfactant and forming the second plurality of spaced-apart droplets comprises providing the droplets of the second plurality of droplets with a second quantity of the second surfactant, wherein the second quantity of the second surfactant differs from the first quantity of the first surfactant.

* * * * *